US005610162A

United States Patent [19]
Witzel et al.

[11] Patent Number: 5,610,162
[45] Date of Patent: Mar. 11, 1997

[54] ESTER DERIVATIVES OF 4-AZA-STEROIDS

[75] Inventors: Bruce E. Witzel, Westfield; Gary H. Rasmusson, Watchung; Richard L. Tolman, Warren; Shu Shu Yang, Bridgewater, all of N.J.

[73] Assignee: Merck & Co., Inc., Rahway, N.J.

[21] Appl. No.: 338,573

[22] PCT Filed: May 19, 1993

[86] PCT No.: PCT/US93/04771

§ 371 Date: Nov. 17, 1994

§ 102(e) Date: Nov. 17, 1994

[87] PCT Pub. No.: WO93/23041

PCT Pub. Date: Nov. 25, 1993

Related U.S. Application Data

[63] Continuation-in-part of Ser. No. 886,022, May 20, 1992, abandoned.

[51] Int. Cl.$^6$ ...................... A61K 31/435; C07D 221/02
[52] U.S. Cl. ................. 514/284; 546/77; 546/78
[58] Field of Search ............................. 514/284; 546/77, 546/78

[56] References Cited

U.S. PATENT DOCUMENTS

| 2,227,876 | 1/1941 | Bolt . |
| 3,239,417 | 3/1966 | DiTullio et al. . |
| 3,264,301 | 8/1966 | Doorenboos . |
| 3,285,918 | 11/1966 | Doorenboos et al. . |
| 4,139,619 | 2/1979 | Chidsey, III . |
| 4,220,775 | 9/1980 | Rasmusson et al. . |
| 4,317,817 | 2/1982 | Blohm . |
| 4,377,584 | 3/1983 | Rasmusson ............................. 546/77 |
| 4,596,812 | 6/1986 | Chidsey, III et al. . |
| 4,732,897 | 3/1988 | Cainelli et al. . |
| 4,760,071 | 7/1988 | Rasmusson et al. . |
| 4,845,104 | 7/1989 | Carlin et al. . |
| 4,859,681 | 8/1989 | Rasmusson et al. . |
| 4,882,319 | 11/1989 | Holt ........................................ 546/77 |
| 4,910,226 | 3/1990 | Holt et al. . |
| 5,049,562 | 9/1991 | Rasmusson et al. ...................... 546/77 |
| 5,110,939 | 5/1992 | Holt et al. ................................ 548/250 |
| 5,116,983 | 5/1992 | Bhattacharya et al. .................... 546/77 |

FOREIGN PATENT DOCUMENTS

| 970692 | of 0000 | Canada . |
| 0200859 | of 0000 | European Pat. Off. . |
| 0155096 | of 0000 | European Pat. Off. . |
| 0004949 | of 0000 | European Pat. Off. . |
| 0314199 | of 0000 | European Pat. Off. . |
| 0289327 | of 0000 | European Pat. Off. . |
| 0277002 | of 0000 | European Pat. Off. . |
| 0343954 | of 0000 | European Pat. Off. . |
| 0375344 | of 0000 | European Pat. Off. . |
| 0375345 | of 0000 | European Pat. Off. . |
| 0375347 | of 0000 | European Pat. Off. . |
| 0375349 | of 0000 | European Pat. Off. . |
| 1465544 | of 0000 | France . |
| WO91/12261 | of 0000 | WIPO . |

OTHER PUBLICATIONS

Doorenbos et al. Jour. Pharm. Sciences, vol. 60 pp. 1234–1235 (1971).
Doorenbos et al. Jour. Pharm. Science vol. 62 pp. 638–640 (1973).
Brooks, Steroids, vol. 47 pp. 1–19 (1986).
Stinson, Chem. & Eng. News Jun. 29, 1992 pp. 7–8.
Burger, Medicinal Chemistry, 2d Ed. Interscience, NY, 1960 p. 42.
Winslow, Wall Street Journal, May 7, 1996 p. B4.
Endo., vol. 91, No. 2, pp. 427–437 (1972) by Neri, et al., "A Biological Profile of a Non–steroidal Antiandrogen, SCH 13521 . . . ".
Steroids, 14, 269–283(1969), by Nayfeh, et al., "Metabolism of Progesterone by Rat Testicular Homogenates–III".
Endo., vol. 92, p.1216 (1973) by Voight & Hsia (See disclosure in Reference AP).
J. Pharm. Sci., 62, No. 4, pp. 638–640 (1973) by Doorenbos & Solomons, "Synthesis & Antimicrobial Properties of 17 Beta–Isopentyloxy–4–Aza–5 Alpha–Androstane and the 4–Methyl Derivative".
J. Pharm. Sci., 60, No. 8, pp. 1234–1235 (1971) by Doorenbos & Brown, "4.17 Alpha–Dimethyl–4–Aza–5 Alpha–Androstan–17 beta–ol Acetate & Related Azasteroids".
J. Pharm., 63, No. 4, pp. 620–622 (1974) by Doorenbos & Kim, "Synthesis & Evaluation of Antimicrobial Properties of Amidinoazaandrostanes and Guanidinoazaandrostanes".
J. Med Chem. (1986) 29 (11): pp. 2298–3115 by Rasmusson, et al., "Aza Steroids: Structure–Activity Relationships . . ".
Prostate (1986) 9 (1): pp. 65–75 by Brooks, et al., "Prostatic Effects Induced in Dogs By . . . 5 alpha–Reductase Inhibitors".
Steroids (1986) 47 (1) pp. 1–19 by Broods, et al., "5 Alpha–Reductase Inhibitory . . . Activities of Some 4–Aza–Steroids in the rat".

(List continued on next page.)

*Primary Examiner*—Donald G. Daus
*Attorney, Agent, or Firm*—Catherine D. Fitch; Joanne M. Giesser; Melvin Winokur

[57] ABSTRACT

Compounds of Formula (I),

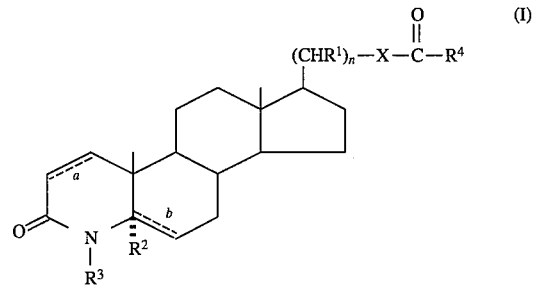

wherein X is sulfur or oxygen are inhibitors of the 5α-reductase enzyme and isozymes thereof. The compounds are useful for the treatment of hyperandrogenic disease conditions and diseases of the skin and scalp.

8 Claims, No Drawings

OTHER PUBLICATIONS

Endocr. (1985) 117 (2): pp. 571–579, by Liang, et al., "Species Differences in Prostatic Steroidal 5 Alpha–Reductases of Rat, Dog and Human".

J. Med. Chem. (1984) 27 (12): pp. 1690–1701, by Rasmusson, et al., "Azasteroids as Inhibitors of Rat Prostatic 5 alpha–reductase".

J. Org. Chem. (1981) vol. 46, No. 7, pp. 1442–1446, T. Back, et al., "N–Chloroazasteroids . . . ".

Chem. Abstracts, vol. 95, 109055j, by T. Liang, et al. "Inhibition of 5 Alpha–Receptor Binding . . . by a 4–Methyl–4–Aza–Steroid".

JNCI, vol. 74, No. 2, pp. 475–481 (Feb. 1985), by N. Kadohama, et al., "Retardation of Prostate Tumor Progression in the Noble Rat by 4–Methyl–4–Aza–Steroidal Inhibitors of 5 Alpha–Reductase".

The Prostate, vol. 10, pp. 189–197 (1987) by G. Andriole, et al., "The Effect of 4MA . . . on the Growth of . . . Human Tumors . . . ".

J. Endocr., vol. 57, pp. 111–121 (1973) by K.D. Bingham, et al., "The Metabolism of Testosterone by Human Male Scalp Skin".

Toxicol. Appl. Pharmacol., vol. 103, pp. 222–227 (1990) by G.L. Kedderis, et al., "Studies With Nitrogen–Containing Steroids . . . ".

Bioinorganic Chemistry, 17, pp. 372–376 (1986) by B. W. Metcalf, et al., "Patent Inhibition of Human Steroid . . . by 3–Androstene–3–Carboxylic Acid".

Biochemistry, 1990, vol. 29, pp. 2815–2824, by M. A. Levy, et al., "Inhibition of Rat Liver Steroid 5 Alpha–Reductase . . . ".

J. Med. Chem., 1990, vol. 33, pp. 943–950, by D. A. Holt, et al. "Steroidal A Ring Carboxylic Acids . . . ".

J. Steroid Biochem., vol. 34, Nos. 1–6, pp. 571–575 (1989), by M. A. Levy, et al., "Interaction Between Rat Prostatec 5 Alpha–Reductase . . . ".

J. Med. Chem., vol. 33, pp. 937–942 (1990) by D. A. Holt, et al., "Steroidal A Ring Aryl Carboxylic Acids".

TIPS, Dec. 1989, vol. 10, pp. 491–495, by D. W. Metcalf, et al., "Inhibitors of . . . 5 Alpha–Reductase in Benign Prostatic Hyperplasia . . . ".

Steroids, vol. 35, No. 3 (Mar. 1980) pp. 1–7, by L. Murphy, et al., "Effect of Estradiol on a . . . Binding Protein in the Uterus of the Mouse".

Prostate, vol. 9, pp. 311–318 (1986) by N. Stone, et al., "Estrogen Formation in Human Prostatic Tissue . . . ".

Steroids, vol. 47, No. 1, pp. 1–19 (1986) by J. R. Brooks, et al., "5 Alpha–Reductase Inhibitiory . . . Activities of Some 4–Azasteroids . . . ".

Lancet, No. 1986, No. 8515, pp. 1095–1096, by F. Labrie, et al. "Combination therapy in prostate cancer".

J. Clin. Endocrin. and Metab., vol. 55, No. 1, pp. 188–193 (1987), by R. Rittmaster, et al., "The Effects of . . . a 5 Alpha–Reductase Inhibitor . . . ".

J. Clin. Endocrin and Metab., vol. 74, No. 2, pp. 345–350 (1990), by A. Diani, et al., "Hair Growth Effects of Oral Administration of Finasteride . . . ".

J. Clin. Endocinol. Metab. 67, No. 4, pp. 808–816 (1988), by N. Bruchovsky, et al., "Kinetic Parameters of 5 Alpha–Reductase Activity in Stroma & Epithelium of Normal Hyperplastic & Carcinomatous Human Prostates".

J. Steroid Biochem. 26, (3) pp. 349–353 (1987), by R. Hudson, "Comparison of Nuclear 5 Alpha–Reductase Activities in the Stromal and Epithelial Fractions of Human Prostatic Tissue".

J. Biol. Chem. 251, (19) pp. 5895–5900 (1976), by R. J. Moore, et al., "Steroid 5 Alpha–Reductase in Cultured Human Fibroblasts".

J. Biol. Chem. 264, (27) pp. 16249–16255 (1989), by S. Andersson, et al., "Expression Cloning & Regulation of steroid 5 alpha–Reductase, an Exzyme Essential for Male Sexual Differentiation".

Proc. Nat'l Acad. Science 87, pp. 3640–3644 (1990), by S. Andersson, et al., "Structural & Biochemical Properties of cloned and expressed human and rat steroid 5 alpha–reductases".

Nature 354, pp. 159–161 (Nov. 14, 1991), by S. Andersson, et al., "Deletion of Steroid 5 Alpha–Reductase–2 Gene in Male Pseudohermaphroditism".

Biol. of Reproduction, vol. 46, pp. 168–173 (1992), by J. D. Wilson, "Syndromes of Androgen Resistance".

Eur. J. Cancer 26(2), p. 188(1990), by A. A.Geldof, et al., "Enzyme Inhibitors in Hormone Dependent Prostate Cancer Growth".

J. Cancer Res. Clin. Oncol. 118, pp. 50–55 (1992), by A. Geldof, et al. "Consideration of the Use of . . . 4MA . . . in Prostate Cancer Therapy".

The Prostate 18, pp. 215–227 (1991), by J. Brooks, et al., "Effect of Castration, DES, Flutamide, and MK–906 on Growth of the Dunning Rat Prostatic Carcinoma . . . ".

Eur. J. Pharm. 183 (5), p. 1757 (1990), by Y. Masubuchi, et al., "Lack of DHT Inhibition . . . by Treatment of 4MA . . . ".

Andriole et al., "Treatment with Finasteride Following Radical Prostatectormy for Prostate Cancer", Urology 45(3):491–497 (1995).

Tsukamoto et al., "Chemoprevention of Rat Prostate Carcinogenesis by Use of Finasteride or Casodex", 87 J. Nat'l Cancer Inst., pp. 842–843 (1995).

Bologna et al, "Antiandrogens and 5–alpha Reductase Inhibition of the Proliferation Rate in PC3 and Du145 Human Prostatic Cancer Cell Lines", 51(6) Cur. Ther. Res., pp. 799–813 (1992).

Doorenbos et al., "4,17alpha–Dimethyl–4–aza–5alpha–androstan–17beta–ol Acetate and Related Azasteroids", J. Pharmaceutical Sciences, vol. 60, No. 8, Aug. 1971, pp. 1234–1235.

ESTER DERIVATIVES OF 4-AZA-STEROIDS

CROSS REFERENCE TO RELATED APPLICATIONS

This application is a national phase application under 35 U.S.C. §371 of PCT application PCT/US93/04771, filed May 19, 1993, which is, in turn, a continuation-in-part of 07/886,022, filed May 20, 1992, now abandoned.

BACKGROUND OF THE INVENTION

The present invention is directed to new 17-position ester and thioester derivatives of 4-azaandrostan-3-ones and related compounds and the use of such compounds as 5α-reductase inhibitors.

The art reveals that certain undesirable physiological manifestations, such as acne vulgaris, seborrhea, female hirsutism, male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., Endo., Vol. 91, No. 2 (1972). However, these products, though devoid of hormonal effects, are peripherally active, competing with the natural androgens for receptor sites, and hence have a tendency to feminize a male host or the male fetus of a female host.

It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation.

A number of 4-aza steroid compounds are known in the art as 5α-reductase inhibitors. For example, See U.S. Pat. Nos. 2,227,876, 3,239,417, 3,264,30and 3,285,918; French Patent No. 1,465,544; Doorenbos and Solomons, J. Pharm. Sci. 62, 4, pp. 638–640 (1973); Doorenbos and Brown, J. Pharm. Sci., 60, 8, pp. 1234–1235 (1971); and Doorenbos and Kim, J. Pharm. Sci. 63, 4, pp. 620–622 (1974).

In addition, U.S. Pat. Nos. 4,377,584, 4,220,775, 4,859,681, 4,760,071 and the articles J. Med. Chem. 27, p. 1690–1701 (1984) and J. Med. Chem. 29, 2998–2315 (1986) of Rasmusson, et al., U.S. Pat. No. 4,845,104 to Carlin, et al., and U.S. Pat. No. 4,732,897 to Cainelli, et al. describe 4-aza-17β-substituted-5α-androstan-3-ones which are said to be useful in the treatment of DHT-related hyperandrogenic conditions.

However, despite the suggestion in the prior art that hyperandrogenic diseases are the result of a single 5α-reductase, there are reports regarding the presence of other 5α-reductase isozymes in both rats and humans. For example, in human prostate, Bruchovsky, et al. (See J. Clin. Endocrinol. Metab. 67, 806–816, 1988) and Hudson (see J. Steroid Biochem. 26, p 349–353, 1987) found different 5α-reductase activities in the stromal and epithelial fractions. Additionally, Moore and Wilson described two distinct human reductases with peaks of activities at either pH 5.5 or pH 7–9. (See J. Biol. Chem. 251, 19, p. 5895–5900, 1976.)

Recently, Andersson and Russell isolated a cDNA which encodes a rat liver 5α-reductase (see J. Biol. Chem. 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1". (See Proc. Nat'l. Acad. Sci. 8.7, p. 3640–3644, 1990.)

More recently, a second, human prostatic reductase (5α-reductase 2) has been cloned with properties identified with the more abundant form found in crude human prostatic extracts. (See Nature, 354, p. 159–161, 1991.)

Further, "Syndromes of Androgen Resistance"—The Biology of Reproduction, Vol. 46, p. 168–173 (1992) by Jean O. Wilson indicates that the 5α-reductase 1 enzyme may be associated with hair follicles.

Thus, the art supports the existence of at least two genes for 5α-reductase and two distinct isozymes of 5α-reductase in humans. Both forms are present in prostatic tissue in which, 5α-reductase 2, is the more abundant, and the other isozyme, 5α-reductase 1, is believed to be more abundant in scalp tissue.

In the treatment of hyperandrogenic disease conditions, e.g. benign prostatic hyperplasia (BPH), it would be desirable to have one drug entity which is active against both enzymes 1 and 2 in the prostate to substantially inhibit dihydrotestosterone (DHT) production. Alternatively, it would be desirable to have a drug entity which is highly selective for inhibiting the scalp associated enzyme 5α-reductase 1, for use in treating diseases of the skin and scalp, e.g. acne and alopecia. The drug could also be used in combination with PROSCAR® (finasteride) which is highly selective for the prostatic enzyme 5α-reductase for combination therapy in the treatment of BPH.

SUMMARY OF THE INVENTION

The present invention discloses novel 17-position ester and thioester derivatives of 4-azaandrostan-3-ones and related compounds which are useful for inhibiting the steroid 5α-reductase enzymes 1 and 2. The compounds are particularly effective in selectively inhibiting the 5α-reductase associated with the scalp, and dually inhibiting both isozymes 1 and 2 in the oral, parenteral or topical-treatment of benign prostatic hyperplasia, acne, female hirsutism, male pattern baldness, androgenic alopecia, prostatitis, and the treatment of prostatic carcinoma.

DETAILED DESCRIPTION

This invention is concerned with compounds of formula I, and combinations thereof for the selective inhibition of 5α-reductase 1 and the combined inhibition of 5α-reductase 1 and 2. Compounds of formula I are defined as follows:

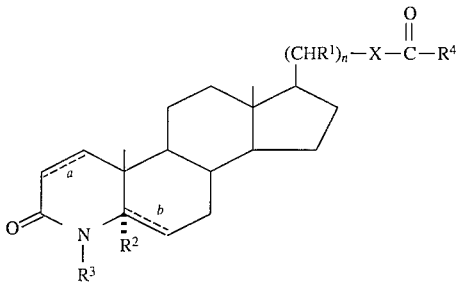

wherein a and b are both single bonds and $R^2$ is hydrogen, or a is a double bond, b is a single bond and $R^2$ is hydrogen, or a is a single bond, b is a double bond and $R^2$ is absent;

$R^1$ is —H, aryl, or —$C_{1-3}$alkyl unsubstituted or substituted with aryl and can be the same or different at each occurrence when n is greater than 1;

$R^3$ is —H, methyl, ethyl, —OH, —$NH_2$ or —$SCH_3$;

n is an integer selected from zero through 10;

X is —O— or —S—; and $R^4$ is

1) —$C_{1-20}$ alkyl, unsubstituted or substituted with one or more of:
 a) —OH,
 b) halo,
 c) —$C_{1-8}$ alkoxy,
 d) —$C_{1-6}$ alkenyl,
 e) —$CONR^5R^5$, wherein $R^5$ is independently
  i) —H,
  ii) —$C_{1-8}$ alkyl unsubstituted or substituted with one or more of $R^7$, aryl or heterocycle, the aryl being unsubstituted or substituted with one or more of $R^7$ or $R^9$,
  iii) aryl unsubstituted or substituted with one or more of $R^7$ or $R^9$, or
  iv) heterocycle, unsubstituted or substituted with one or more of $R^7$ or $R^9$,
 f) —$COOR^6$, wherein $R^6$ is
  i) —H,
  ii) —$C_{1-8}$ alkyl unsubstituted or substituted with one or more of $R^7$ or aryl, the aryl being unsubstituted or substituted with one or more of $R^7$ or $R^9$, or
  iii) aryl unsubstituted or substituted with one or more of $R^7$ or $R^9$,
 g) —$S(O)_p$—$R^5$, wherein p is zero, 1 or 2;
 h) —$N(R^5)_2$,
 i) aryl, unsubstituted or substituted with one or more of aryl, $R^7$ or $R^9$,
 j) heterocycle, unsubstituted or substituted with one or more of $R^7$ or $R^9$,
 k) —$C_{3-10}$ cycloalkyl, such as cyclohexyl, norbornyl, or adamantyl, unsubstituted or substituted with one or more of $R^7$ or $R^9$, or
 1) $CONR^8$—CO—$NHR^8$, wherein $R^8$ is —H, —$C_{1-8}$ alkyl, benzyl or cyclohexyl,
2) aryl, unsubstituted or substituted with one or more of aryl, $R^7$ or $R^9$,
3) heterocycle or —$C_{3-10}$ cycloalkyl, either of which is unsubstituted or substituted with one or more of $R^7$ or $R^9$,
4) —$NRSR^5$, or
5) —$O^5$;

$R^7$ is
 1) —OH,
 2) —$C_{1-3}$ alkoxy,
 3) —CN,
 4) —$COOR^6$,
 5) —$C_{1-8}$alkyl—$COOR^6$,
 6) —$NO_2$, or
 7) halo; and
 8) amino, mono-$C_1$-$C_4$alkylamino, di-$C_1$-$C_4$ alkylamino;

$R^9$ is
 1) —$C_{1-8}$ alkyl, unsubstituted or substituted with one or more of aryl or $R^7$,
 2) —CO—A, —$C_{1-8}$ alkyl—CO—A, —NHCO—A, or —$S(O)_p$—A, wherein p is defined above and A is
  a) —H,
  b) —$C_{1-8}$ alkyl, unsubstituted or substituted with one or more of
   i) —$R^7$, or
   ii) aryl, unsubstituted or substituted with one or more of $R^7$, or
  c) aryl, unsubstituted or substituted with one or more of $R^7$,
 3) —NHCO-heterocycle,
 4) —$N(R^{10})_2$ or —$CON(R^{10})_2$ wherein $R^{10}$ is independently, heterocycle or —A,
 5) —HNCO—$(CH_2)_q$—CO—Q, wherein q is 1–4, and Q is —$N(R^{10})_2$ or —$OR^{10}$;

with the provisos that:

when n is 1–10, b is a single bond, $R^1$ is —H at each occurrence, X is —O—, and $R^4$ is —$C_{1-6}$alkyl, $R^4$ is not substituted with an unsubstituted phenyl ring;

when n is 1–10, b is a single bond, $R^1$ is —H at each occurrence, and X is —O—, $R^4$ is not unsubstituted $C_{5-10}$cycloalkyl, unsubstituted phenyl, amino, —$C_{1-8}$alkyl substituted amino, or —$C_{1-8}$alkoxy;

when n is zero, X is —O—, a and h are both single bonds and $R^3$ is —H, then $R^4$ is not —$CH_3$; and when n is 1, $R^1$ is —$C_3$, X is —O—, a and b are both single bonds, and $R^3$ is —H, then $R^4$ is not —$CH_3$;

or a pharmaceutically acceptable salt or ester thereof.

A first preferred embodiment of this invention is represented by compounds of formula II

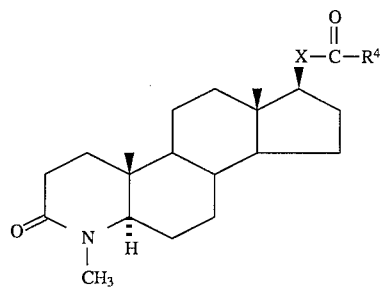

wherein $R^4$ is —$C_{1-20}$alkyl, unsubstituted or substituted with one or more of OH, halo —$C_{1-8}$alkoxy, —$C_{1-6}$alkenyl, —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, p, $R^5$ $R^7$ and $R^9$ are all as defined in formula I.

A second preferred embodiment of this invention is represented by compounds of formula II wherein $R^4$ is —$C_{1-20}$ alkyl substituted with —$CONR^5R^5$, —$COOR^6$ or —$CONR^8CONHR^8$, and X, $R^5$, $R^6$, and $R^8$ are all as defined in formula I.

A third preferred embodiment of this invention is represented by compounds of formula II wherein $R^4$ is aryl unsubstituted or substituted with one or more of aryl, $R^7$ or $R^9$;

heterocycle unsubstituted or substituted with one or more of $R^7$ or $R^9$;

—$C_{3-10}$ cycloalkyl unsubstituted or substituted with one or more of $R^7$ or $R^9$;

—$NR^5R^5$; or —$OR^5$; and X, $R^5$, $R^7$, and $R^9$ are all as defined in formula I.

A fourth preferred embodiment of this invention is represented by compounds of formula III

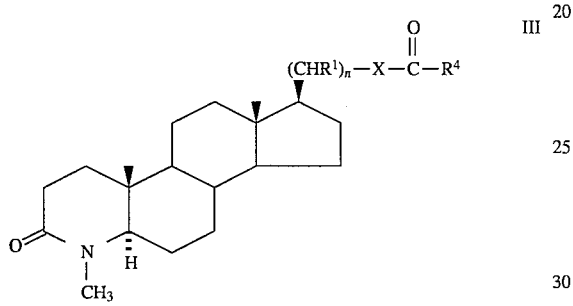

wherein $R^4$ is —$C_{1-20}$ alkyl, unsubstituted or substituted with one or more of —OH halo —$C_{1-8}$alkoxy, —$C_{1-6}$alkenyl —$S(O)_p$—$R^5$, —$N(R^5)_2$, aryl unsubstituted or substituted with one or more of aryl, $R^7$ or $R^9$, heterocycle unsubstituted or substituted with one or more of $R^7$ or $R^9$, or —$C_{3-10}$ cycloalkyl unsubstituted or substituted with one or more of $R^7$ or $R^9$, and X, n, p, $R^1$, $R^5$, $R^7$, and $R^9$ are all as defined in formula I.

A fifth preferred embodiment of this invention is represented by compounds of formula III wherein $R^a$ is —$C_{1-20}$ alkyl substituted with —$CONR^5R^5$, —$COOR^6$ or —$CONR^8CONHR^8$, and X, n, $R^1$, $R^5$, $R^6$, and $R^8$ are all as defined in formula I.

A sixth preferred embodiment of this invention is represented by compounds of formula III wherein $R^4$ is aryl unsubstituted or substituted with one or more of aryl, $R^7$ or $R^9$;

heterocycle unsubstituted or substituted with one or more of $R^7$ or $R^9$;

—$C_{3-10}$ cycloalkyl unsubstituted or substituted with one or more of $R^7$ or $R^9$;

—$NR^5R^5$; or —$OR^5$;

and X, n, $R^1$, $R^5$, $R^7$, and $R^9$ are all as defined in formula I.

Unless other wise specified, the 17-substituent is assumed to be in the beta configuration.

Novel compounds of the present invention include but are not limited to the following compounds:

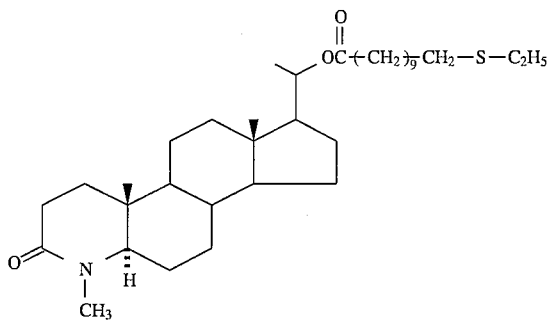

20-(11-(ethylthio)undecanoyloxy)-4-methyl-5α-4-azapregnan-3-one,

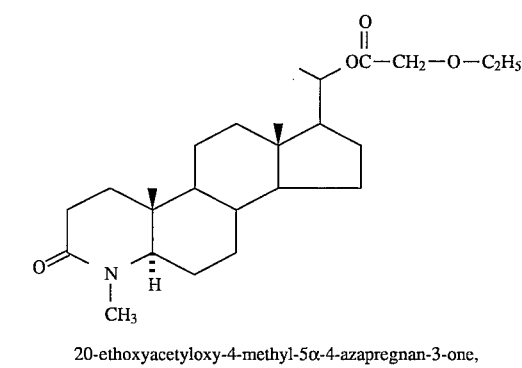

20-ethoxyacetyloxy-4-methyl-5α-4-azapregnan-3-one,

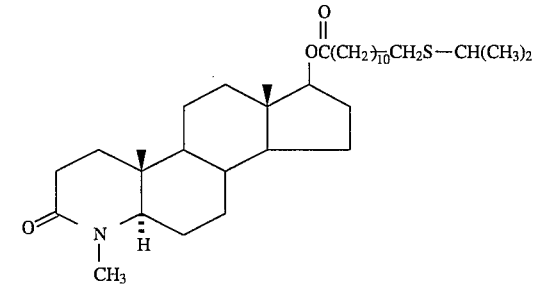

17-(12-(isopropylthio)dodecanoyloxy)-4-methyl-5α-4-azaandrostan-3-one,

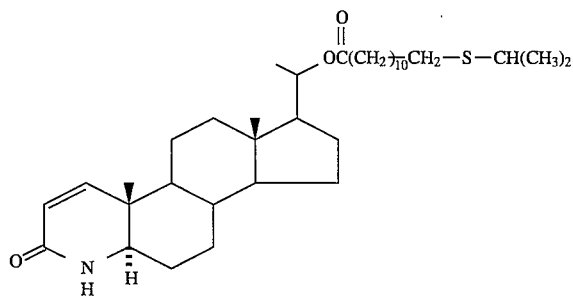

20-(12-(isopropylthio)-dodecanoyloxy)-5α-4-azapregn-1-ene-3-one,

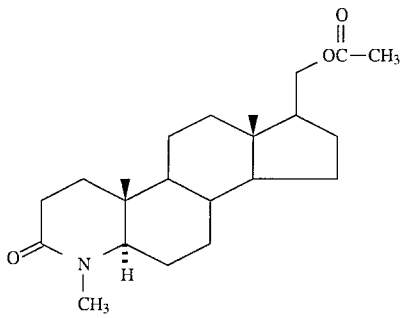

17-acetyloxymethyl-4-methyl-5α-4-azaandrostan-3-one, 4-methyl-20-tridecanoyloxy-5α-4-azapregnan-3-one,
20-t-butylacetyloxy-4-methyl-5α-4-azapregnan-3-one,
4-methyl-20-trimethylacetyloxy-5α-4-azapregnan-3-one,
4-methyl-20-(10-undecenoyloxy)-5α-4-azapregnan-3-one,
20-(3,7-dimethyl-6-octenoyloxy)-4-methyl-5α-azapregnan-3-one,
20-(3-carboxypropionyloxy)-4-methyl-5α-4-azapregnan-3-one,
20-(11-(carbomethoxy)undecanoyloxy)-4-methyl-5α-4-azapregnan-3-one,
20-(3-(carbobenzyloxy)propionyloxy)-4-methyl-5α-4-azapregnan-3-one,
20-(1-adamantylacetyloxy)-4-methyl-5α-4-azapregnan-3-one
4-methyl-20-(2-norbornylacetyloxy)-5α-4-azapregnan-3-one,
20-(3,4-dimethoxyphenyl)acetyloxy-a-methyl-5α-4-azapregnan-3-one,
20-(4-isopropylphenyl)acetyloxy-4-methyl-5α-4-azapregnan-3-one
20-(isopropylthio)acetyloxy-4-methyl-5α-4-azapregnan-3-one,
20-(9-(isopropylthio)nonanoyloxy)-4-methyl-5α-4-azapregnan-3-one,
20-(12-(isopropylthio)dodecanoyloxy)-4-methyl-5α-4-azapregnan-3-one, 20-(11-(ethylsulfinyl)undecanoyloxy)-4-methyl-5α-4-azapregnan-3-one,
20-(12-(t-butylthio)dodecanoyloxy)-4-methyl-5α-4-azapregnan-3-one
4-methyl-20-(4-(thien-2-yl))butyroyloxy-5α-4-azapregnan-3-one,
20-trimethylacetyloxy-5α-4-azapregnan-3-one,
20-(9-(isopropylthio)nonanoyloxy)-5α-4-azapregnan-3-one,
20-(12-(isopropylthio)dodecanoyloxy)-5α-4-azapregnan-3-one,
20-acetoxymethyl-4-methyl-5α-4-azapregnan-3-one,
4-methyl-20-(trimethylacetyloxy)methyl-5α-4-azapregnan-3-one,
20-(12-(isopropylthio)dodecanoyloxy)methyl-4-methyl-5α-4-azapregnan-3-one,
4-methyl-17-trimethylacetyloxymethyl-5α-4-azaandrostan-3-one,
17-(2-ethylhexanoyloxy)methyl-4-methyl-5α-4-azaandrostan-3-one,
17-(12-(isopropylthio)dodecanoyloxy)methyl-4-methyl-5α-4-azaandrostan-3-one,
20-trimethylacetyloxy-5α-4-azapregn-1-ene-3-one,
17β-(benzylaminocarbonyloxy)-4-methyl-5α-4-azaandrostan-3-one,
20-(t-butylaminocarbonyloxy)-4-methyl-5α-4-azapregnan-3-one,
17-(t-butylaminocarbonyloxymethyl)-4-methyl-5α-4-azaandrostan-3-one or
17-(methylaminocarbonyloxymethyl)-4-methyl-5α-4-azaandrostan-3-one.

Novel compounds of the present invention further include, but are not limited to the following compounds:
17-(2-furylacetoxymethyl)-4-methyl-5α-4-azaandrostan-3-one,
17-(4-isopropylphenylacetoxymethyl)-4-methyl-5α-4-azaandrostan-3-one,
17-(cyclohexylacetoxymethyl)-4-methyl-5α-4-azaandrostan-3-one,
17-(3-indolylacetoxymethyl)-4-methyl-5α-4-azaandrostan-3-one,
17-(4-methylcyclohexanecarbonyloxymethyl)-4-methyl-5α-4-azaandrostan-3-one,
17-(4-(3-indolyl)-butyryloxymethyl)-4-methyl-5α-4-azaandrostan-3-one,
17-(4-isobutylbenzoyloxymethyl)-4-methyl-5α-4-azaandrostan-3-one,
17-(acetoxyacetyloxymethyl)-4-methyl-5α-4-azaandrostan-3-one,
17-(6-bromohexanoyloxymethyl)-4-methyl-5α-4-azaandrostan-3-one,
4-methyl-20-(4-nitrobenzoyloxymethyl)-5α-4-azapregnan-3-one,
20-((3-acetamido)benzoyloxy)-4-methyl-5α-4-azapregnan-3-one,
20-(3,4-dimethoxyphenylacetyloxymethyl)-4-methyl-5α-4-azapregnan-3-one,
17-(4-ethoxybenzoyloxymethyl)-4-methyl-5α-4-azaandrostan-3-one,
4-methyl-20-(palmitoyloxymethyl)-5α-4-azapregnan-3-one,
17-(iminodibenzyl-5-carbonyloxymethyl)-4-methyl-5α-4-azaandrostan-3-one,
4-methyl-20-(stearoyloxy)-5α-4-azapregnan-3-one,
17-(3,5-bis-(trifluoromethyl)benzoyloxymethyl)-4-methyl-5α-4-azaandrostan-3-one,
17-(3-cyanobenzoyloxymethyl)-4-methyl-5α-4-azaandrostan-3-one,
20-(heptafluorobutyryloxymethyl)-4-methyl-5α-4-azapregnan-3-one,
20-(4-benzoylbenzoyloxymethyl)-4-methyl-5α-4-azapregnan-3-one,
17-(benztriazol-5-carbonyloxymethyl)-4-methyl-5α-4-azaandrostan-3-one,
20-(3,5-difluorobenzoyloxy)-4-methyl-5α-4-azapregnan-3-one,
17-(bis-(4-isopropyl)phenyl)acetyloxymethyl-4-methyl-5α-4-azaandrostan-3-one,
4-methyl-20-(salicylyloxymethyl)-5α-4-azapregnan-3-one,
17-((3-hydroxy-4,4,4-trichlorobutyryloxy)methyl)-4-methyl-5α-4-azaandrostan-3-one, or
17-(cinnamoyloxymethyl)-4-methyl-5α-4-azaandrostan-3-one.

Also included within the scope of this invention are pharmaceutically acceptable salts or esters, where a basic or acidic group is present in a compound of formula I, such as on the substituted alkyl, cycloalkyl, aryl or heterocyclic moiety. When an acidic substituent is present, i.e. —COOH, there can be formed the ammonium, sodium, potassium, calcium salt, and the like, for use as the dosage form.

Where a basic group is present, i.e. amino, acidic salts, i.e. hydrochloride, hydrobromide, acetate, pamoate, and the like, can be used as the dosage form.

Also, in the case of the —COOH group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention, may have asymmetric centers and occur as racemates, racemic mixtures and as individual diastereomers, with all isomeric forms being included in the present invention.

When any variable (e.g., aryl, heterocycle, $R^1$ $R^2$ n X etc.) occurs more than one time in any constituent or in formula I, II or III its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge. "Cycloalkyl" is intended to include saturated mono-, bi- and tricyclic ring groups, such as cyclopropyl, cyclobutyl, cyclopentyl, cyclohexyl (Cyh), cycloheptyl, norbornanyl and adamantyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Halo", as used herein, means fluoro, chloro, bromo and iodo.

As used herein, with exceptions as noted, "aryl" is intended to mean phenyl (Ph) or naphthyl.

The term heterocycle or heterocyclic, as used herein except where noted, represents a stable 5- to 7-membered monocyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazol idinyl, isoxazolyl, isoxazolidinyl, morpholinyl, thiazolyl, thiazoli dinyl, isothiazolyl, quinuclidinyl, isothiazolidinyl, indolyl, quinolinyl, isoquinolinyl, benzimid, azolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl. Preferred heterocycles are piperidinyl, 2-oxopyrrolodinyl, pyrrolyl, pyrazolyl, imidazolyl, pyridyl, pyrazinyl, pyrimidinyl, pyridazinyl, oxazolyl, isoxazolyl, morpholinyl, thiazolyl, isothiazolyl, quinuclidinyl, indolyl, quinolinyl, isoquinolinyl, benzimidazolyl, thiadiazoyl, benzothiazolyl, benzoxazolyl, furyl, tetrahydrofuryl, thienyl, and benzothienyl.

"M.p." or "mp" is an abbreviation for melting point; "m.w." or "mw" is an abbreviation for molecular weight.

The compounds of the present invention are made by methods well known to those skilled in the art. The compounds of this invention are generally made from asteroid alcohol starting material, represented. by formula (i)

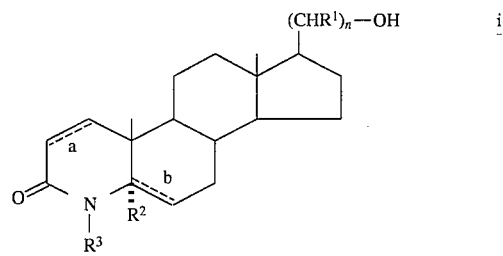

wherein
a and b are both single bonds and $R^2$ is hydrogen, or
a is a double bond, b is a single bond and $R^2$ is hydrogen, or
a is a single bond, b is a double bond and $R^2$ is absent;
$R^1$ is —H, aryl, or $C_{1-3}$alkyl unsubstituted or substituted with aryl and where n is greater than 1, $R^1$ can be the same or different; $R^3$ is —H, methyl or ethyl; and n is an integer from zero through 10.

Methods of making starting alcohols of formula (i) are well known to those skilled in the art, and are described, for example, in the following publications: Rasmusson, G. H. et al., *J. Med. Chem.*, 29, 2298–2315 (1986); Rasmusson, G. H. et al., *J. Med. Chem.*, 27, 1690–1701 (1984).

Furthermore, the starting 4-azasteroid-20 alcohols of Formula (i) may be made by several methods well known to those skilled in the art. For example, 4-azasteroids containing a 17-carbonyl group (e.g. carboxaldehyde) may be reacted with the appropriate organo-metallic reagent to yield the corresponding secondary alcohol, while reduction yields the primary alcohol. Also, an appropriate 17-ketone may be reduced (e.g. with sodium borohydride) to the desired alcohol. The above mentioned ketones may be made by several methods well known in the art; one particularly useful method is that of A. Bhattacharya et al., Synthetic Communications 20(17), 2683–2690 (1990), in which an activated carbonyl compound is reacted with a suitable Grignard reagent to give the desired ketone. Other activated carbonyl compounds (e.g. pyridine thioesters) may also be used.

These alcohol functions may be constructed both before and after the formation of the 4-aza moiety.

One method of preparing compounds of formula I is to condense the starting steroid alcohol with an acid of formula (ii)

under conditions known to those skilled in the art, e.g., in an appropriate solvent such as $CH_2Cl_2$, in the presence of 4-(dimethylamino)-pyridine (DMAP) and N,N'-dicyclohexylcarbodiimide (DCC).

Another method of preparing compounds of formula I is to combine the starting alcohol (i) with an acid chloride of formula (iii) or acid anhydride or mixed anhydride of formula (iv)

under conditions known to those skilled in the art, e.g. under dry conditions using an appropriate solvent such as $CH_2C_2$ at e.g. reduced temperature, such as about 0° C., in the presence of a base such as pyridine.

Carbamate derivatives of formula I can be prepared by reacting the starting alcohol (i) with an isocyanate compound, such as benzyl isocyanate or t-butylisocyanate for example, under conditions known to those skilled in the art, e.g., under dry conditions in an appropriate solvent such as benzene, in the presence of a base such as pyridine or 1,4-diazabicyclo[2.2.2]octane, or in the case of a hindered isocyanate such as t-butylisocyanate, 1,8-diazabicyclo [5.4.0]undec-7-ene (DBU), with heating e.g. to 60°–70° C., or at room temperature.

The thiol esters may be conveniently prepared from the corresponding alcohol via the literature procedure described in Tetrahedron Letters, 22 (1981) pp. 3119–3122, that is, the alcohol and a thiolacid are reacted together in the presence of the preformed adduct from triphenylphosphine and diisopropyl azodicarboxylate. Alternatively, the free thiol obtained from these thiolesters via standard saponification or reduction methods may then be acylated via standard procedures to obtain other thiolesters.

The variable "$R^4$" used in the above synthetic method descriptions is defined in formula I, and is independently defined at each occurrence in formula (iv).

Accordingly, the present invention is particularly concerned with providing a method of treating the hyperandrogenic conditions of androgenic alopecia, acne vulgaris, seborrhea, benign prostatic hyperplasia, prostatitis, the treatment of prostatic carcinoma, by oral, parenteral or typical administration, of the novel compounds of the present invention.

The present invention is thus also concerned with providing suitable topical, oral and parenteral pharmaceutical formulations for use in the novel methods of treatment of the present invention.

The compositions containing the compounds of the present invention as the active ingredient for use in the treatment of e.g., benign prostatic hypertrophy, prostatitis, and prostatic carcinoma, and-hyperandrogenic conditions can be administered in a wide variety of therapeutic dosage forms in conventional vehicles for systemic administration, as, for example, by oral administration in the form of tablets, capsules, solutions, or suspensions, of by injection. The daily dosage of the products may be varied over a wide range varying from 0.5 to 1,000 mg per adult human/per day. The compositions are preferably provided in the form of scored tablets containing 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.002 mg. to about 50 mg./kg. of body weight per day. Preferably the range is from about 0.01 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calciuim phosphate, lactose, corn starch or magnesium stearate. The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservative are employed when intravenous administration is desired.

For the treatment of androgenic alopecia, acne vulgaris, seborrhea, female hirsutism, the compounds of the present invention are administered in a pharmaceutical composition comprising the active compound in combination with a pharmacologically acceptable carrier adapted for topical administration. Parenteral or oral administration are also applicable. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The following examples are illustrative of representative embodiments of this invention and should not be construed to be limits on the scope or spirit of the instant invention.

The fast atom bombardment (FAB) and electron impact (EI) mass spectral (MS) values are reported as molecular ion peaks and are indicated as either $M^+$, $M^{+1}$, $M^{-1}$ or $M^{+2}$ being the molecular weight (mw) the molecular weight plus one atomic mass unit, the molecular weight minus one atomic mass unit, or the molecular weight plus two atomic mass units.

The $^1H$ nuclear magnetic resonance (NMR) data was taken at 200 or 400 MHz and is tabulated for unique proton values of each compound at the end of the Examples.

EXAMPLE 1

Preparation of 20-(11-(ethylthio)undecanoyloxy)-4-methyl-5α-a-azapregnan-3-one

To a stirred solution of 20-hydroxy-4-methyl-5α-4-azapregnan-3-one (0.66 g, 2.0 mM), 11-ethylthioundecanoic acid (0.493 g, 2.0 mM), and 4-(dimethylamino)-pyridine 0.242 g, 2.0 mM) in methylene chloride (25 mL) was added N,N'-dicyclohexylcarbodiimide (0.48 g, 2.3 mM) in methylene chloride (3 mL plus 2×3 mL rinses) at room temperature. After stirring overnight two times, the mixture was filtered from the precipitated dicyclohexylurea and concentrated, and the residue flash chromatographed on silica gel using ethyl acetate as eluant to yield the title compound as a thick oil. MS $M^{+1}$ calculated for $C_{34}H_{59}NO_3S$, mw=561, 90; observed m/e 562.

EXAMPLE 2

Preparation of 20-ethoxyacetyloxy-4-methyl-5α-4-azapregnan-3-one

Employing substantially the same procedure as described in Example 1, but substituting ethoxyacetic acid in place of the ethylthioundecanoic acid used therein, the title compound is obtained.

EXAMPLE 3

Preparation of 17-(12-(isopropylthio)dodecanoyloxy)-4-methyl-5α-4-azaandrostan-3-one Employing substantially the same procedure as described in Example 1, but substituting 17-hydroxy-4-methyl-5α-4-azaandrostan-3-one and 12-(isopropylthio)dodecanoic acid for the 20-hydroxy-4-methyl-5α-4-azapregnan-3-one and 11-ethylthioundecanoic acid, respectively, used therein, the title compound was obtained. MS $M^+$ calculated for $C_{34}H_{59}NO_3S$, mw=561.92; observed m/e 561.

EXAMPLE 4

Preparation of a) 20-(9-(isopropylthio)nonanoyloxy)-5α-4-azapregnan-3-one and b) 20-(12-(isopropylthio)dodecanoyloxy)-5α-4-azapregn-1-ene-3-one Employing substantially the same procedure as described in Example 1, but substituting the steroid alcohol and acid starting materials used therein with the following compounds, both of the title compounds were obtained:

Title compound a): 20-hydroxy-5α-4-azapregnan-3-one and 9-(isopropylthio)nonanoic acid. MS M$^+$calculated for $C_{32}H_{55}NO_3S$, mw=533.85; observed m/e 533;

Title compound b): 20-hydroxy-5α-4-azapregn-1-ene-3-one and 12-(isopropylthio)dodecanoic acid. MS M$^+$ calculated for $C_{35}H_{59}NO_3S$, mw=573.92; observed m/e 573.

EXAMPLE 5

Compounds of formula 3, below, were made employing substantially the same procedure as described in Example 1, but substituting the compounds of formula 1 and 2, below, in place of the 20-hydroxy-4-methyl-5α-4-azapregnan-3-one and 11-ethylthioundecanoic acid respectively, used therein.

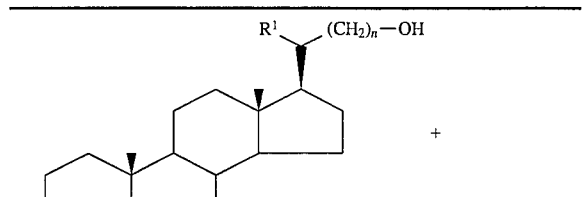

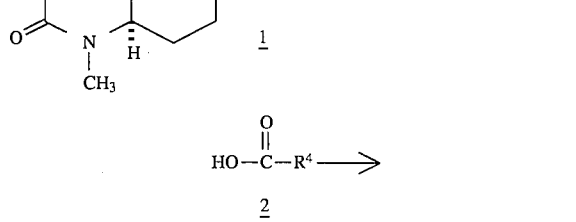

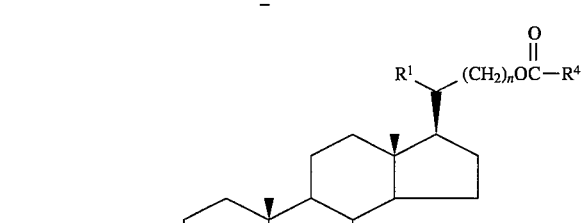

| | R$^1$ | n | R$^4$ |
|---|---|---|---|
| a) | —CH$_3$ | zero | —(CH$_2$)$_{11}$CH$_3$ |
| b) | —CH$_3$ | zero | —CH$_2$CH(CH$_3$)CH$_2$CH$_2$CH=C(CH$_3$)$_2$ |
| c) | —CH$_3$ | zero | —CH$_2$-1-adamantyl |
| d) | —CH$_3$ | zero | —CH$_2$-2-norbornyl |
| e) | —CH$_3$ | zero | 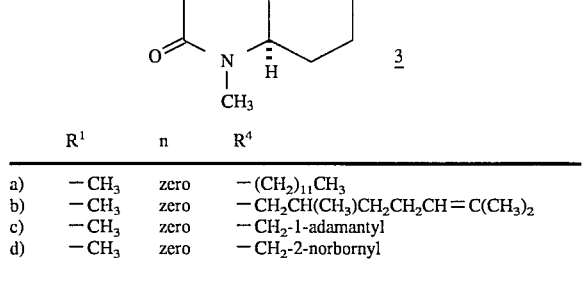 |

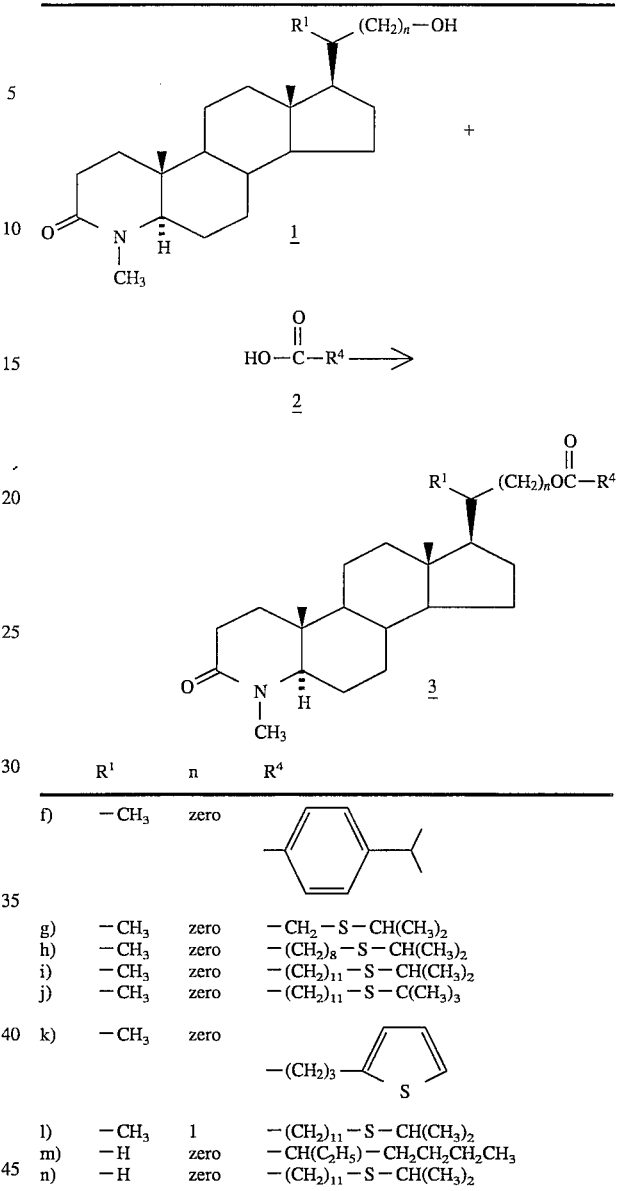

| | R$^1$ | n | R$^4$ |
|---|---|---|---|
| f) | —CH$_3$ | zero | (p-isopropylphenyl) |
| g) | —CH$_3$ | zero | —CH$_2$—S—CH(CH$_3$)$_2$ |
| h) | —CH$_3$ | zero | —(CH$_2$)$_8$—S—CH(CH$_3$)$_2$ |
| i) | —CH$_3$ | zero | —(CH$_2$)$_{11}$—S—CH(CH$_3$)$_2$ |
| j) | —CH$_3$ | zero | —(CH$_2$)$_{11}$—S—C(CH$_3$)$_3$ |
| k) | —CH$_3$ | zero | —(CH$_2$)$_3$-(thienyl) |
| l) | —CH$_3$ | 1 | —(CH$_2$)$_{11}$—S—CH(CH$_3$)$_2$ |
| m) | —H | zero | —CH(C$_2$H$_5$)—CH$_2$CH$_2$CH$_2$CH$_3$ |
| n) | —H | zero | —(CH$_2$)$_{11}$—S—CH(CH$_3$)$_2$ |

The compounds above have the following corresponding mass spectral data:

a) MS M$^+$ calculated for $C_{34}H_{59}NO_3$, mw=529.85; observed. m/e 529;

b) MS M$^+$ calculated for $C_{31}H_{51}NO_3$, mw=485 75; observed m/e 485;

c) MS M$^+$ calculated for $C_{33}H_{51}NO_3$, mw=509 78; observed m/e 509;

d) MS M$^+$ calculated for $C_{30}H_{47}NO_3$, mw=469 71; observed m/e 469;

e) MS M$^+$ calculated for $C_{31}H_{45}NO_5$; mw=511 71; observed m/e 511;

f) MS M$^+$ calculated for $C_{31}H_{45}NO_3$; mw=479 71; observed m/e 479;

g) MS M$^+$ calculated for $C_{26}H_{43}NO_3S$; mw=449.69; observed m/e 449;

h) MS M$^+$ calculated for $C_{33}H_{57}NO_3S$; mw=547.88; observed m/e 548;

i) MS M⁺ calculated for $C_{36}H_{63}NO_3S$; mw=589.94; observed m/e 589;

j) MS M⁺¹ calculated for $C_{37}H_{65}NO_3S$; mw=604.00; observed m/e 605;

k) MS M⁺¹ calculated for $C_{29}H_{43}NO_3S$; mw=485.73; observed m/e 486;

l) MS M⁻¹ calculated for $C_{37}H_{65}NO_3S$; mw=604.00; observed m/e 603;

m) MS M⁺ calculated for $C_{28}H_{47}NO_3S$; mw=445.69; observed m/e 445;

n) MS M⁺ calculated for $C_{35}H_{51}NO_3S$; mw=575.92; observed m/e 575.

EXAMPLE 6

Preparation of 4-methyl-20-(10-undecenoyloxy)-5α-4-azapregnan-3-one

To a solution of 20-hydroxy-4-methyl-5α-4-azapregnan-3-one (0.167 g, 0.5 mM) and pyridine (0.1 mL) in anhydrous methylene chloride (4.5 mL) at ice-bath temperatures was added 10-undecenoyl chloride (0.13 mL, 0.6 mM) dropwise. After 10 minutes, the reaction mixture was allowed to warm to room temperature and stir overnight. After diluting further with methylene chloride the mixture was washed with dilute hydrochloric acid, water, and brine, and dried ($Na_2SO_4$). The residue obtained from concentration of the filtered solution was flash chromatographed on silica gel using ethyl acetate as eluant to give the title compound as a glaze. MS M⁺ calculated for $C_{32}H_{53}NO_3$, mw=499.78; observed m/e 499.

EXAMPLE 7

Compounds of formula 6, below, were made employing substantially the same procedure as described in Example 6, but substituting the compounds of formula 4 and 5, below, in place of the 20-hydroxy-4-methyl-5α-4-azapregnan-3-one and 10-undecenoyl chloride, respectively, used therein.

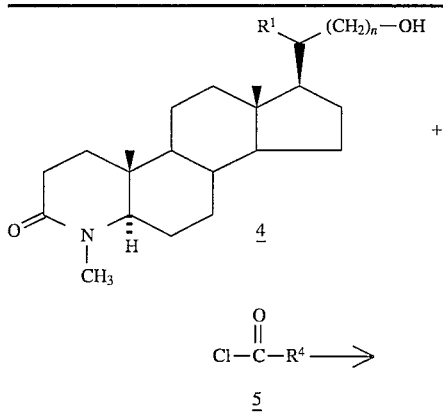

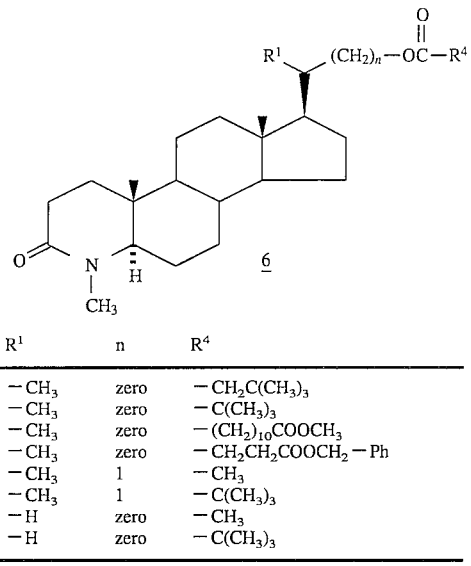

| | R¹ | n | R⁴ |
|---|---|---|---|
| a) | —CH₃ | zero | —CH₂C(CH₃)₃ |
| b) | —CH₃ | zero | —C(CH₃)₃ |
| c) | —CH₃ | zero | —(CH₂)₁₀COOCH₃ |
| d) | —CH₃ | zero | —CH₂CH₂COOCH₂—Ph |
| e) | —CH₃ | 1 | —CH₃ |
| f) | —CH₃ | 1 | —C(CH₃)₃ |
| g) | —H | zero | —CH₃ |
| h) | —H | zero | —C(CH₃)₃ |

The compounds above have the following corresponding mass spectral data:

a) MS M⁺ calculated for $C_{27}H_{45}NO_3$, mw=431.67; observed m/e 431;

b) MS M⁺¹ calculated for $C_{26}H_{43}NO_3$, mw=417.64; observed m/e 418;

c) MS M⁺ calculated for $C_{34}H_{57}NO_5$; mw=559.84; observed m/e 559;

d) MS M⁺² calculated for $C_{32}H_{45}NO_5$; mw=523.72; observed m/e 525;

e) ME M⁺ calculated for $C_{24}H_{39}NO_3$; mw=389.59; observed m/e 389;

f) MS M⁺ calculated for $C_{27}H_{45}NO_3$; mw=431.67; observed m/e 431;

g) MS M⁺ calculated for $C_{22}H_{35}NO_3$; mw=361.53; observed m/e 361;

h) MS M⁺ calculated for $C_{25}H_{41}NO_3$; mw=403.61; observed m/e 403.

EXAMPLE 8

Preparation of 20-trimethylacetyloxy-5α-4-azapregn-1-ene-3-one

Employing substantially the same procedure as described in Example 6, but substituting 20-hydroxy-5α-4-azapregn-1-ene-3-one and trimethylacetyl chloride for the 20-hydroxy-4-methyl-5α-4-azapregnan-3-one and 10-undecenoyl chloride, respectively, used therein, the title compound was obtained. MS M⁻¹ calculated for $C_{25}H_{39}NO_3$, mw=402.53; observed m/e 401.

EXAMPLE 9

Preparation of 20-(11-(ethylsulfinyl)undecanoyloxy)-4-methyl-5α-4-azapregnan-3-one To a stirred solution of 20-(11-(ethylthio)undecanoyloxy)-4-methyl-5α-4-azapregnan-3-one (0.056 g, 0.1 mM) in acetone (5 mL) at room temperature was added a solution of sodium periodate (0.033 mg, 0.154mM) in water (3 drops). After prolonged stirring with additional portions of the periodate added (0.046 g total) over 3 days, the solvents were removed in vacuo, and the residue extracted with

EXAMPLE 10

Preparation of 17β-(benzylaminocarbonyloxy)-4-methyl-5α-4-azaandrostan-3-one methylene chloride. The methylene chloride was removed in vacuo, and the resulting residue was flash chromatographed on silica gel (30% acetone/methylene chloride eluant) to give the title compound as a glaze. MS M$^+$ calculated for $C_{34}H_{59}NO_4S$, mw=577.90; observed m/e 577.

EXAMPLE 10

Preparation of 17β-(benzylaminocarbonyloxy)-4-methyl-5α-4-azaandrostan-3-one

To a solution of 17B-hydroxy-4-methyl-5α-4-azaandrostan-3-one (61 mg) in pyridine (0.60 ml) was added benzyl isocyanate (54 mg, 0.40 mmol). The mixture was stirred at 60°–70° C. under $N_2$ for 18 hr and pumped in vacuo to remove pyridine. The residue was purified using a silica gel plate (2000μ) developed with ethyl acetate (Rf=0.37, run in EtOAc) to give the title compound; m.p. is 216°–217° C.

EXAMPLE 11

Preparation of 20-(3-carboxypropionyloxy)-4-methyl-5α-4-azapregnan-3-one 20-(3-(Carbobenzyloxy>propionyloxy)-4-methyl-5α-4-azapregnan-3-one (0.05 g, 0.095 mM) was reduced with hydrogen in ethyl acetate in the presence of 5% palladium on carbon, to obtain the title compound. MS M$^{+1}$ calculated for $C_{25}H_{39}NO_5$, mw=433.64; observed m/e 434.

EXAMPLE 12

Preparation of 20-(acetylthiomethyl)-4-methyl-5α-4-azapregnan-3-one

By reacting 20-(hydroxymethyl)-4-methyl-5α-4-azapregnan-3-one with thioacetic acid as per the procedure of *Tetrahedron Letters* 22 (1981) pp. 119–3122, the title compound is obtained.

EXAMPLE 13

Preparation of 17-(t-butylaminocarbonyloxymethyl)-4-methyl-5α-4-azaandrostan-3-one To a stirred solution of 17-(hydroxymethyl)-4-methyl-5α-4-azaandrostan-3-one (0.048 g, 0.15 mM) in dried benzene (5 mL) was added at room temperature t-butylisocyanate (0.03 mL, 0.23mM) followed by 1,8-diazabicyclo[5.4.0]undec-7-ene (DBU) (0.023 mL, 0.15 mM). After stirring for two days, the volatiles were removed in vacuo and the residue flash chromatographed on silica gel using ethyl acetate as eluant to give the title compound as a white solid. MS M$^{+1}$ calculated for $C_{25}H_{42}N_2O_3$, mw=418.55; observed m/e 419.

EXAMPLE 14

Preparation of 20-(t-butylaminocarbonylory)-4-methyl-5α-4-azapregnan-3-one

Employing substantially the same procedure as described in Example 13, but substituting 20-hydroxy-4-methyl-5α-4-azapregnan-3-one for the steroid alcohol used therein, the title compound was obtained. MS M$^{+1}$ calculated for $C_{26}H_{44}N_2O_3$, mw=432.65; observed m/e 433.

EXAMPLE 15

Preparation of 17-(methylaminocarbonyloxymethyl)-4-methyl-5α-4-azaandrostan-3-one Employing substantially the same procedure as described in Example 10, but substituting methyl isocyanate and 17-(hydroxymethyl)-4-methyl-5α-4-azaandrostan-3-one for the benzyl isocyanate and steroid alcohol, respectively, used therein, the title compound was obtained. MS M$^+$2 calculated for $C_{22}H_{36}N_2O_3$, mw=376.54; observed m/e 378.

Also included with the scope of this invention are 4-N—X analogs where X is OH, $NH_2$ or $SCH_3$. The 4-NO—H and 4-N—$NH_2$ derivatives can be made by incorporating hydroxylamine or hydrazine, respectively, in place of methyl amine in the seco acid ring A closure for the starting androstanes herein as described in J. Med. Chem. 29, 2998–2315 (1986) by Rasmusson et al. Further, reaction of the anion of the saturated 4-N—H androstanes, wherein the anion is generated from the 4-NH precursor by sodium hydride, and methylsulfenyl chloride can produce the corresponding 4-N—$SCH_3$ derivative. Thus, substituent $R^3$ on the 4-N position also includes OH, $NH_2$ and $SCH_3$.

| | NMR DATA (ppm) | |
|---|---|---|
| Example | Angular Methyls | Miscellaneous |
| 1 | 0.64, 0.88 | 2.94 (-4-NC$\underline{H}_3$) |
| 3 | 0.81, 0.91 | 1.24 (—SCH(C$\underline{H}_3$)$_2$) |
| | | 1.28 |
| 4a | 0.64, 0.90 | 1.25 (—SCH(C$\underline{H}_3$)$_2$) |
| | | 1.28 |
| 4b | 0.64, 0.94 | 1.22 (—SCH(C$\underline{H}_3$)$_2$) |
| | | 1.26 |
| 5a | 0.64, 0.88 | 2.95 (-4-NC$\underline{H}_3$) |
| 5b | 0.62, 0.86 | 2.92 (-4-NC$\underline{H}_3$) |
| 5c | 0.62, 0.87 | 2.92 (-4-NC$\underline{H}_3$) |
| 5d | 0.64, 0.88 | 2.92"(-4-NC$\underline{H}_3$) |
| 5e | 0.59, 0.88 | 3.80 (Ph—(OC$\underline{H}_3$)$_2$) (Split) |
| 5f | 0.65, 0.82 | 1.22 (Ph—CH(C$\underline{H}_3$)$_2$) |
| | | 1.25 |
| 5g | 0.65, 0.88 | 3.21 (—SC$\underline{H}_2$CO$_2$—) |
| 5h | 0.63, 0.88 | 1.24 (—SCH(C$\underline{H}_3$)$_2$) |
| | | 1.28 |
| 5i | 0.63, 0.87 | 1.24 (—SCH(C$\underline{H}_3$)$_2$) |
| | | 1.27 |
| 5j | 0.64, 0.88 | 1.30 (—C(C$\underline{H}_3$)$_3$ |
| 5k | 0.64, 0.88 | 2.92 (-4-NC$\underline{H}_3$) |
| 5l | 0.70, 0.88 | 1.24 (—SCH(C$\underline{H}_3$)$_2$) |
| | | 1.26 |
| 5m | 0.63, 0.85 | 2.89 (-4-NC$\underline{H}_3$) |
| 5n | 0.67, 0.89 | 2.93 (-4-NC$\underline{H}_3$) |
| 6 | 0.64, 0.88 | 2.92 (-4-NC$\underline{H}_3$) |
| 7a | 0.64, 0.88 | 1.02 (—C(C$\underline{H}_3$)$_3$) |
| 7b | 0.64, 0.87 | 1.13 (—C(C$\underline{H}_3$)$_3$) |
| 7c | 0.64, 0.88 | 3.66 (—CO$_2$C$\underline{H}_3$) |
| 7d | 0.62, 0.87 | 5.14 (—OC$\underline{H}_2$Ph) |
| 7e | 0.69, 0.88 | 2.04 (—OCOC$\underline{H}_3$) |
| 7f | 0.70, 0.88 | 1.20 (—C(C$\underline{H}_3$)$_3$) |
| 7g | 0.66, 0.90 | 2.02 (—OCOC$\underline{H}_3$) |
| 7h | 0.68, 0.89 | 1.18 (—C(C$\underline{H}_3$)$_3$) |
| 8 | 0.64, 0.94 | 1.16 (—C(C$\underline{H}_3$)$_3$) |
| 9 | 0.62, 0.88 | 2.94 (-4-NC$\underline{H}_3$) |
| 10 | 0.89, 0.92 | 2.94 (-4-NC$\underline{H}_3$) |
| 11 | 0.62, 0.86 | 2.92 (-4-NC$\underline{H}_3$) |
| 13 | 0.64, 0.86 | 1.29 (—OCONH—C(C$\underline{H}_3$)$_3$) |
| 14 | 0.69, 0.89 | 1.32 (—OCONH—C(C$\underline{H}_3$)$_3$) |
| 15 | 0.67, 0.88 | 2.78 (—OCONH—C$\underline{H}_3$) |
| | | 2.82 |

Novel compounds of the present invention further include, but are not limited to, the following compounds:
20-(t-butylaminocarbonyloxy)-4-methyl-5-α-4-azapregnan-3-one, 20-(isopropylaminocarbonyloxy)-4-methyl-5-α-4-azapregnan-3-one, 17-((2-ethylphenylamino)carbonyloxymethyl)-4-methyl-5-α-4-azaandrostan-3-one, 4-methyl-20-(methylaminocarbonyloxy)-5-α-4-azapregnan-3-one, and 24-(t-butylaminocarbonyloxy)-4-methyl-5-α-4-aza-cholan-3-one.

These compounds can be prepared using substantially the same procedures as described in Example 14, using the appropriate starting materials.

Furthermore, the present invention discloses compounds of formula I-a, useful for dually inhibiting both steroid 5α-reductase enzymes 1 and 2 and selectively inhibiting 5α-reductase 1,

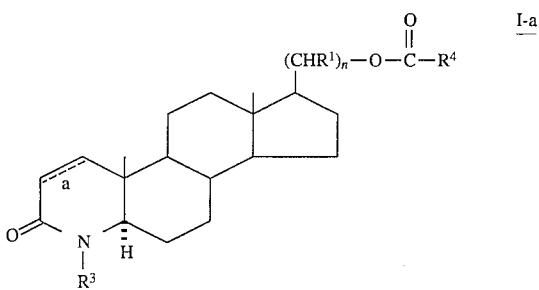

wherein:

(I) a is single bond;

$R^1$ is H;

$R^3$ is —H, methyl, ethyl, —OH, —NH$_2$, or —SCH$_3$;

n is an integer selected from 1 through 10; and $R^4$ is

1) —C$_{1-6}$ alkyl substituted with an unsubstituted phenyl ring, 2) unsubstituted C$_{5-10}$ cycloalkyl, 3) unsubstituted phenyl, 4) amino, 5) —C$_{1-8}$ alkyl substituted amino, or 6 —C$_{1-8}$ alkoxy;

(II) a is a single bond;

$R^3$ is —H;

n is zero; and $R^4$ is —CH$_3$; or (III) a is a single bond;

$R^1$ is —CH$_3$;

$R^3$ is —H;

n is 1; and $R^4$ is —CH$_3$;

or a pharmaceutically acceptable salt or ester thereof.

BIOLOGICAL ASSAYS

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay.

The reaction mixture contained in a final volume of 100 μl is: 40 mM buffer (human scalp, potassium phosphate, pH 6.5;human prostatic 5α-reductase, sodium citrate, pH 5.5), 0.3–10 μM $^{14}$C-T (or $^3$H-T) ("T" stands for testosterone), 1 mM DTT, and 500 μM NADPH. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A auto-sampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Stumptail macaque protocol

The following protocol is utilized with the stumptail macaque monkey to demonstrate the effect of compounds of the present invention for promoting hair growth.

Twenty-one male stumptail macaque monkeys of species *Macaca speciosa* are assigned to vehicle control and drug treatment groups on the basis of baseline hair weight data. This assignment procedure is necessary to insure that the average baseline hair growth for each control and experimental group is comparable. The control and drug treatment groups are as follows:

1. Topical 50:30:20 vehicle (N=6)
2. Oral 5α-reductase and topical 50:30:20 vehicle (N=5)
3. Oral placebo (N=5)
4. 5α-reductase in vehicle (N=5)

The vehicle consists of 50% propylene glycol, 30% ethanol and 20% water. A 100 mM concentration of topical 5α-reductase is formulated in this vehicle. The same 5α-reductase is administered as an oral dose of 0.5 mg per monkey. Immediately prior to the dosing phase of the study, hair is removed from a 1 inch square area (identified by four tatoos) in the center of the balding scalp. This hair collection is the baseline hair growth determination prior to the beginning of treatment. Approximately 250 μL of vehicle and 5α-reductase in vehicle is prepared and topically administered to the tatooed area of the scalp. The selected 5α-reductase and placebo is ingested by the monkeys at the same time as the topical doses are administered. The monkeys are dosed once per day, seven days per week for twenty weeks.

At four week intervals throughout the dosing phase of the study, each monkey is shaved and the hair is collected and weighed. The body weight data (at baseline and during assay) is analyzed by the monparametric Wilcoxon rank-sum test. Differences are significant at p<0.05. Hair weight data at each week collection for vehicle, placebo and treatment groups are expressed as the change from baseline. Statistical analysis is performed on the rank of the data to show overall differences among groups at each four week collection.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of formula I

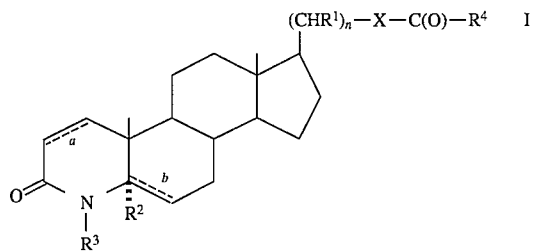

wherein "a" and "b" are both single bonds and $R^2$ is hydrogen, or "a" is a double bond, "b" is a single bond and $R^2$ is hydrogen, or "a" is a single bond, "b" is a double bond and $R^2$ is absent;

$R^1$ can be the same or different at each occurrence when n is greater than 1 and is selected from —H, aryl, and —$C_{1-3}$alkyl unsubstituted or substituted with aryl;

$R^3$ is —H, methyl, ethyl, —OH, —$NH_2$ or —$SCH_3$;

n is an integer selected from zero to 10;

X is —O— or —S—;

$R^4$ is
(1) —$NR^5R^5$;

$R^5$ is independently selected from the group consisting of
(i) —H,
(ii) —$C_{1-8}$alkyl unsubstituted or substituted with one of $R^7$, aryl or heterocycle, the aryl being unsubstituted or substituted with one of $R^7$ or $R^9$,
(iii) aryl unsubstituted or substituted with one of $R^7$ or $R^9$, or
(iv) heterocycle, unsubstituted or substituted with one of $R^7$ or $R^9$;

$R^7$ is selected from
(1) —OH,
(2) —$C_{1-3}$alkoxy,
(3) —CN,
(4) —$COOR^6$,
(5) —$C_{1-8}$alkyl-$COOR^6$
(6) —$NO_2$,
(7) -halo; and
(8) amino, mono-$C_1$–$C_4$-alkylamino, di-$C_1$–$C_4$-alkylamino;

$R^9$ is
(1) —$C_{1-8}$alkyl, unsubstituted or substituted with one or two or three of aryl or $R^7$,
(2) —CO—A, —$C_{1-8}$alkyl-CO—A, —NHCO—A, or —$S(O)_p$—A, wherein p is zero, 1 or 2, and A is
(a) —H,
(b) —$C_{1-8}$alkyl, unsubstituted or substituted with one of
(i) —$R^7$, or
(ii) aryl, unsubstituted or substituted with one of $R^7$, or
(c) aryl, unsubstituted or substituted with one of $R^7$,
(3) —NHCO-heterocycle,
(4) —$N(R^{10})_2$ or —$CON(R^{10})_2$ wherein $R^{10}$ is independently heterocycle or —A,
(5) —NHCO—$(CH_2)_q$—CO—Q, wherein q is an integer from 1–4, and Q is —$N(R^{10})_2$ or —$OR^{10}$;

aryl is phenyl or naphthyl;

heterocycle is piperidinyl, 2-oxopiperidinyl, 2-oxopyrrolodinyl, pyrrolyl, 4-piperidonyl, pyrrolidinyl, pyrazolyl, pyrazolidinyl, imidazolyl, imidazolinyl, imidazolidinyl, pyridyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, thienyl, benzothienyl, or oxadiazolyl;

or a pharmaceutically acceptable salt or ester thereof, where the ester is acetate, maleate or pivaloyloxymethyl.

2. The compound of claim 1 having structural formula II

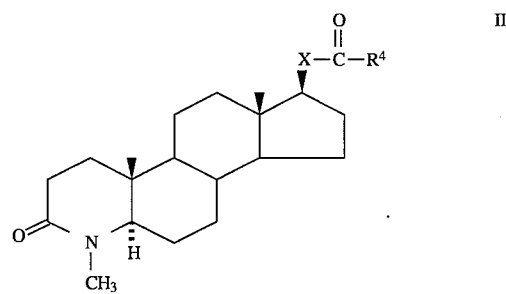

3. The compound of claim 1 having structural formula III

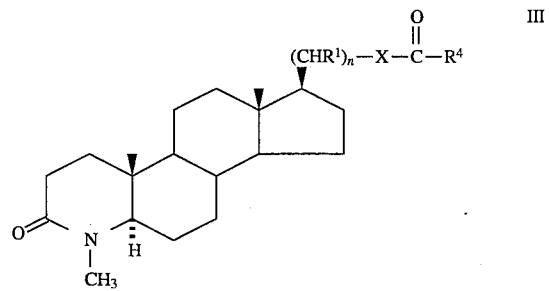

4. A compound of formula I-a

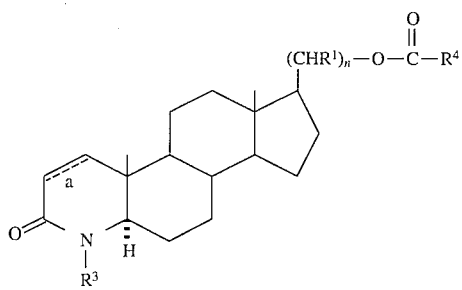

wherein:
"a" is a single or double bond;
$R^1$ is —H;
$R^3$ is —H, methyl, ethyl, —OH, —$NH_2$, or —$SCH_3$;
n is an integer selected from 1 through 10; and
$R^4$ is
  (1) amino, or
  (2) —$C_{1-8}$alkyl substituted amino;
or a pharmaceutically acceptable salt or ester thereof.

5. A compound selected from the group consisting of:
17-(t-butylaminocarbonyloxymethyl)-4-methyl-5α-4-azaandrostan-3-one,
17-(methylaminocarbonyloxymethyl)-4-methyl-5α-4-azaandrostan-3-one, and
20-(t-butylaminocarbonyloxy)-4-methyl-5α-4-azapregnan-3-one,
or a pharmaceutically acceptable salt or ester thereof.

6. A compound selected from the group consisting of:
20-(t-butylaminocarbonyloxy)-4-methyl-5-α-4-azapregnan-3-one,
20-(isopropylaminocarbonyloxy)-4-methyl-5-α-4-azapregnan-3-one,
17-((2-ethylphenylamino)carbonyloxymethyl)-4-methyl-5-α-4-azaandrostan-3-one,
4-methyl-20-(methylaminocarbonyloxy)-5-α-4-azapregnan-3-one, and
24-(t-butylaminocarbonyloxy)-4-methyl-5-α-4-azacholan-3-one,
or a pharmaceutically acceptable salt thereof.

7. A pharmaceutical composition comprising 0.5 to 1000 mg of a compound of claim 1 in a pharmaceutically acceptable carrier therefor.

8. The use of a compound of claim 1 for the preparation of a medicament useful for treating benign prostatic hyperplasia, acne, and female hirsutism, in a human host in need of such treatment.

* * * * *

UNITED STATES PATENT AND TRADEMARK OFFICE
CERTIFICATE OF CORRECTION

PATENT NO. : 5,610,162

DATED : March 11, 1997

INVENTOR(S) : B.E. Witzel et al.

It is certified that error appears in the above-identified patent and that said Letters Patent is hereby corrected as shown below:

At Column 22, line 30, delete "morpholinyl".

Amend Claim 8 as follows:

-- 8. The use of a compound of Claim 1 [for the preparation of a medicament useful for treating benign prostatic hyperplasia, acne, and female hirsutism,] for treating acne in a human host in need of such treatment. --

Signed and Sealed this

Eighth Day of July, 1997

Attest:

BRUCE LEHMAN

Attesting Officer

Commissioner of Patents and Trademarks